(12) United States Patent
Bettsworth et al.

(10) Patent No.: US 11,193,929 B2
(45) Date of Patent: Dec. 7, 2021

(54) SYNTHETIC BI-EPITOPE COMPOUND

(71) Applicant: BIOMERIEUX, Marcy l'etoile (FR)

(72) Inventors: Florence Bettsworth, Dommartin (FR); Sandrine Busseret, Lyons (FR); Catherine Pothion, Lyons (FR)

(73) Assignee: BIOMERIEUX, Marcy l'Etoile (FR)

( * ) Notice: Subject to any disclaimer, the term of this patent is extended or adjusted under 35 U.S.C. 154(b) by 213 days.

(21) Appl. No.: 15/531,901

(22) PCT Filed: Dec. 17, 2015

(86) PCT No.: PCT/FR2015/053560
§ 371 (c)(1),
(2) Date: May 31, 2017

(87) PCT Pub. No.: WO2016/097613
PCT Pub. Date: Jun. 23, 2016

(65) Prior Publication Data
US 2017/0269070 A1    Sep. 21, 2017

(30) Foreign Application Priority Data

Dec. 18, 2014  (FR) ...................................... 1462709

(51) Int. Cl.
| | | |
|---|---|---|
| G01N 33/53 | (2006.01) | |
| G01N 33/96 | (2006.01) | |
| C07K 14/47 | (2006.01) | |
| G01N 33/68 | (2006.01) | |
| G01N 33/531 | (2006.01) | |

(52) U.S. Cl.
CPC ......... *G01N 33/5308* (2013.01); *C07K 14/47* (2013.01); *C07K 14/4716* (2013.01); *C07K 14/4723* (2013.01); *G01N 33/53* (2013.01); *G01N 33/531* (2013.01); *G01N 33/6887* (2013.01); *G01N 33/96* (2013.01); *G01N 2333/4712* (2013.01); *G01N 2800/32* (2013.01)

(58) Field of Classification Search
CPC ............... C07K 14/47; C07K 14/4716; C07K 14/4723; G01N 2333/4712; G01N 2800/32; G01N 33/53; G01N 33/5308; G01N 33/531; G01N 33/6887; G01N 33/96
See application file for complete search history.

(56) References Cited

U.S. PATENT DOCUMENTS

| | | | | |
|---|---|---|---|---|
| 5,846,738 A | * | 12/1998 | Seidel ................ | C07K 14/4716 435/7.1 |
| 6,114,180 A | | 9/2000 | Doth et al. | |
| 2008/0305512 A1 | * | 12/2008 | Mattingly ........ | G01N 33/54326 435/28 |
| 2013/0330744 A1 | * | 12/2013 | Da Silva ............ | G01N 33/6887 435/7.92 |

FOREIGN PATENT DOCUMENTS

| | | |
|---|---|---|
| EP | 0650053 A1 | 4/1995 |
| FR | 2756827 A1 | 6/1998 |
| FR | 2781802 A1 | 2/2000 |
| WO | 95/08000 A2 | 3/1995 |
| WO | 98/24816 A1 | 6/1998 |
| WO | 2010/112777 A1 | 10/2010 |

OTHER PUBLICATIONS

Philibert et al., "A focused antibody library for selecting scFvs expressed at high levels in the cytoplasm," BMC Biotechnology, 2007, 7:81, the total number of pp. 17.*
Gonzales et al., "SDR grafting of murine antibody using multiple human germline templates to minimize its immunogenicity," Mol. Immunol., 2004, vol. 41, pp. 863-872.*
Nominé et al., "Antibody Binding Selectivity: Alternative Sets of Antigen Residues Entail High-Affinity Recognition," PLoS One, 2015, 10(12): e0143374, the total number of pp. 20.*
Nasal et al., "An Intramolecular Disulfide Bridge between Cys-7 and Cys61 Determines the Structure of the Secretory Core Gene Product (e Antigen) of Hepatitis B Virus," J. Virol., 1993, pp. 4307-4315.*
A printout retrieved from http://www.bapeks.com/page/10&category=9&qPage=3 on Jun. 12, 2019.*
A printout retrieved from https://www.hiv.lanl.gov/content/immunology/tables/ab_summary.html on Jan. 23, 2020.*
Szurdoki et al., "Important Factors in Hapten Design and Enzyme-Linked Immunosorbent Assay Development," in Immunoanalysis of Agrochemicals; Nelson, J., et al.; ACS Symposium Series, 1995, vol. 586, Chapter 4, pp. 39-63.*
Lloyd et al., "Modelling the human immune response: performance of a 1011 human antibody repertoire against a broad panel of therapeutically relevant antigens," Protein Engineering, Design & Selection, 2009, vol. 22, No. 3, pp. 159-168.*

(Continued)

*Primary Examiner* — Galina M. Yakovleva
(74) *Attorney, Agent, or Firm* — Oliff PLC

(57) ABSTRACT

A bi-epitope compound of formula I:

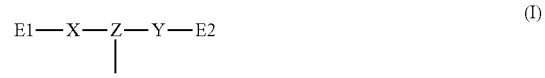

in which: E1 and E2, identical or different, each separately represents a peptide sequence including at least one epitope of an analyte; X and Y, identical or different, each separately represents a linking arm, the carrier molecule is soluble and Z represents an amino acid derivative bearing a thiol function prior to the bonding of same with the carrier molecule. The compound may be contained in a composition, used as a control or standard in an immunoassay and associated method, and/or provided in a kit for implementing an immunoassay.

7 Claims, 3 Drawing Sheets
Specification includes a Sequence Listing.

(56) References Cited

OTHER PUBLICATIONS

Kage et al., "Role of Cys-603 in dimer/oligomer formation of the breast cancer resistance protein BCRP/ABCG2," Cancer Sci., 2005, vol. 96, No. 12, pp. 866-872.*
Gilsdorf et al., "Reactivity of Antibodies against Conserved Regions of Pilins of Haemophilus influenzaeType b," J. Infectious Diseases, 1993, vol. 167, No. 4, pp. 962-965.*
Boresma, YL et al., "DARPins and other repeat protein scaffolds: advances in engineering and applications," Current Opinion in Biotechnology, 2011, vol. 22, pp. 849-857.
Ellington, Ad et al., "In vitro selection of RNA molecules that bind specifc ligands," Nature, 1990, vol. 346, pp. 818-822.
Merrifield, R.B et al., "Solid Phase Peptide Synthesis I. The Synthesis of a Tetrapeptide," J Am Chem Soc., Jul. 20, 1963, vol. 85, pp. 2149-2154.
Hillson, David A. et al., "Resolution of Thiol-Containing Proteins By Sequenital-Elution Covalent Chromatography," Journal of Biochemical and Biophysical methods, 1981, vol. 4 No. 2, pp. 101-111.
Schellinger, Joan G. et al., "A general chemical synthesis platform for crosslinking multivalent single chain variable fragments," Organic & Biomolecular Chemistry, 2012, vol. 10, No. 8 pp. 1521-1526.
Laure, Catherine et al., "New Monoclonal Antibodies As Probes For Human Cardiac Troponin I: Epitopic Analysis With Synthetic Peptides," Molecular Immunology, 1992, vol. 29, No. 2, pp. 271-278.
Fields, Gregg B. et al. "Solid phase peptide synthesis utilizing 9-fluorenylmethoxycarbonyl amino acids," Int. J. Peptide Protein Res, 1990, vol. 35, pp. 161-214.

* cited by examiner

SYNTHETIC BI-EPITOPE COMPOUND

REFERENCE TO AN ELECTRONIC SEQUENCE LISTING

The contents of the electronic Sequence Listing (Sequence_Listing.txt; size: 6,134.8 bytes; date of creation: Jun. 29, 2020) is herein incorporated by reference in its entirety.

The present invention relates to the field of diagnosis or prognosis. In particular, it relates to a synthetic bi-epitope compound that is of use during the implementation of immunoassays.

Immunoassays are commonly used in the fields of clinical, food, pharmaceutical and chemical analyses. Thus, their objective is to determine the presence of a large number of analytes, in the form of proteins (antigens/antibodies), peptides or haptens, for instance steroids or vitamins, in a sample that may contain these analytes. The immunoassay is a test widely known to those skilled in the art which involves immunological reactions between the analyte to be detected and one or more binding partner(s) for this analyte. By way of example of such immunoassays, mention may be made of methods such as ELISA (Enzyme Linked Immuno Sorbent Assay), ELFA (Enzyme Linked Fluorescent Assay) and RIA (Radio Immuno Assay) which can operate according to the "sandwich" principle, or else according to the "competition" principle, and immunodetection methods such as immunohistochemistry, immunocytochemistry, immunofluorescence, Western blot and dot blot. The "competition" methods are normally used for small molecules such as haptens, the "sandwich" methods being used for the other analytes.

These immunoassays carried out in particular in biological test laboratories require the provision, by the manufacturer, in addition to the reagents required for the test, such as the binding partners, the revealing agents or else the diluting solutions, of a positive control for the test which, used under conditions analogous to those of the test for the sample to be studied, often simultaneously, will serve to validate that the immunoassay has performed correctly. If the positive control is indeed found to be positive, the result of the test is validated and can be interpreted. If the positive control is not found to be positive, this indicates that the implementation of the immunoassay did not take place in compliance with expectations. The result of the test which is invalid should then not be interpreted and the analysis should be recommenced.

With regard to the quantification of an analyte by immunoassay in a biological sample that may contain said analyte, it requires, in addition to the abovementioned reagents required for the test and the positive control, the use of a standard curve. Said curve is obtained i) by measuring the signal generated by standards, also called calibrators, which correspond to increasing and known amounts or concentrations of the analyte or of a compound having the same antigenic reactivity as the analyte in the immunoassay used, ii) and then in plotting the curve giving the signal as a function of the amount or the concentration. Very often, it is standard practice to find a mathematical model which represents, as reliably as possible, this relationship between the signal and the amount or concentration, in order to be able to easily calculate the results of a quantitative immunoassay.

To do this, the control or standard solutions must mimic the analyte sought and be recognized in the same way by the binding partners used in the immunoassay. Thus, if the method of the immunoassay is a sandwich method, the control or standard solutions must comprise a compound which has the two epitopes for recognition of the two binding partners used. The term "bi-epitope compound" is then used.

It is not out of the question for the two epitopes of a bi-epitope compound to be identical. When the analyte to be detected or quantified is multimeric, at least dimeric, it is possible to use the same binding partner in capture and in detection of the sandwich immunoassay. In this case, the bi-epitope compound will contain the same epitope twice.

The control or standard solutions normally used in immunoassay tests may be of human or animal origin and may contain the analyte as such in the natural state. These solutions are prepared from lyophilizate, and frozen in unit doses and stored at −20° C. or −80° C. Such storage is not suitable for fluid laboratory practice. Furthermore, these lyophilized control or standard solutions need to be redissolved in order for it to be possible for them to be used. However, in the immunoassay context, the implementation of the test must be rapid and this redissolving results in a loss of time. Furthermore, the performing of this redissolving can lead to a measurement error because of a bias due to the dilution. Ready-to-use control or standard solutions, stored in liquid form at +2/8° C., are thus particularly recommended, this being for obvious reasons of convenience. Nevertheless, in order to be representative of the actual conditions of the assay, these ready-to-use control or standard solutions contain only low concentrations of the analyte, for example about one pg/ml, one ng/ml or one µg/mL, depending on the range of measurement of the analyte concerned, which results in their stability at a temperature of +2/8° C. being affected. Consequently, in order to overcome this drawback, synthetic standards have been used.

European patent application EP 0 650 053A describes synthetic standards containing active sites for one or more receptors, linked to one another by an arborescent structure. This application describes more specially troponin T synthetic standards. Nevertheless, these standards have a stability time in solution which does not exceed 3 weeks at 4° C.

Patent application WO 98/24816, for its part, provides synthetic bi-epitope compounds that can be used as a standard in "sandwich" immunoassays, for assaying troponin I, and that are stable for several months. The compounds described, of formula $\Sigma$-E1-4-E2-$\Psi$, comprise two peptide sequences E1 and E2 comprising a minimum troponin I epitope, each of these epitopes being bonded to one another by a linker group 2 which can be a central peptide comprising from 1 to 40 amino acids. Each epitope can also comprise at its end a peptide sequence of 1 to 10 amino acids ($\Sigma$ and $\Psi$). Nevertheless, the solution proposed in this patent application has the drawback that the bi-epitope compounds described, in order to be sufficiently immunoreactive with the binding partners used in the immunoassay, must have a not insignificant number of amino acids, such that they are not easy to synthesize. Furthermore, by virtue of their uniquely peptide nature, a large quantity of compound is required in the control or standard solution in order to have optimal immunoreactivity with the binding partners used in the immunoassay, which represents a not insignificant cost for the manufacturer of kits containing this control or this standard and thus for the laboratory which uses the kit thus produced.

U.S. Pat. No. 6,114,180 proposes, for its part, a synthetic compound that can be used as a control or standard in immunoassays comprising two troponin I epitopes linked to one another by a carrier molecule, such as BSA, with the objective of increasing its solubility and/or its stability in solution. However, the particular construction of this compound makes it difficult to produce and raises the question of the equimolarity between the two epitopes linked to the carrier molecule.

The applicant has demonstrated, surprisingly, a synthetic compound to be used in "sandwich" immunoassays which overcomes the drawbacks described in the prior art. Indeed, its synthesis is easy and simplified, it is stable at +2/8° C. and at low concentration, it is soluble and it exhibits excellent immunoreactivity with the binding partners used in the immunoassay. Furthermore, it is not necessary to use a large amount thereof, if the compound is present in the control or standard solution, to have optimal immunoreactivity with the binding partners used in the immunoassay. Finally, the construction of the compound according to the invention guarantees the equimolarity of the two epitopes at certain Thus, the first subject of the present invention is a bi-epitope compound of formula (I):

(I)

in which:

E1 and E2, which may be identical or different, each independently represent a peptide sequence comprising at least one epitope of an analyte, X and Y, which may be identical or different, each independently represent a linker arm, the carrier molecule is soluble and Z represents an amino acid derivative bearing a thiol function before the bonding thereof with the carrier molecule.

Another subject of the invention relates to a composition containing a compound of formula I in solution in water, in a buffer or in a biological fluid.

Yet another subject relates to the use of such a bi-epitope compound or of such a composition containing this compound as a control or standard or adjuster in an immunoassay.

Yet another subject of the invention relates to the immunoassay processes using, as a control and/or standard or adjuster, a bi-epitope compound of formula I or a composition containing this compound.

Finally, the last subject of the present invention is a kit for implementing an immunoassay, comprising a bi-epitope compound of formula (I) or a composition containing such a compound.

The applicant has thus developed, against all expectations, a synthetic bi-epitope compound which makes it possible to overcome all the drawbacks of the prior art mentioned above. The compound of the invention has formula (I) below:

(I)

in which:

E1 and E2, which may be identical or different, each independently represent a peptide sequence comprising at least one epitope of an analyte;

X and Y, which may be identical or different, each independently represent a linker arm, the carrier molecule is soluble and Z represents an amino acid derivative bearing a thiol function before the bonding thereof with the carrier molecule.

The compound of the invention is thus a bi-epitope compound. The term "bi-epitope compound" is intended to mean a compound which comprises two epitopes of one and the same analyte in order to mimic the antigenic recognition of said analyte in a sandwich immunoassay. Of course, the synthetic bi-epitope compound in no way consists of the same sequence as the analyte that it mimics. This synthetic compound does not therefore correspond to a sequence of amino acids that exist naturally, for example a protein or a protein fragment. The compound of the invention will be referred to, in an obvious and equivalent manner throughout the application, as bi-epitope compound, non-natural bi-epitope compound, synthetic bi-epitope compound or non-natural synthetic bi-epitope compound.

The prefix "immuno" in the term "immunoassay", for example, should not be considered in the present application as strictly indicating that the binding partner is necessarily a partner of immunological origin, such as an antibody or an antibody fragment. Indeed, as is well known to those skilled in the art, this term is more widely used to also denote tests and processes in which the binding partner is not a partner of immunological origin/nature but consists, for example, of a receptor of the analyte that it is desired to detect and/or quantify. Whatever its origin or its nature, the binder partner concerned should be capable of binding to the analyte sought, preferably specifically. Thus, it is known practice to use the term "ELISA assay" for assays which use binding partners that are non-immunological in the strict sense, also widely known as "ligand binding assay", whereas the term "immuno" is included in the term in extenso corresponding to the acronym ELISA. In the interests of clarity and uniformity, the term "immuno" is used in the present application to denote any biological analysis using at least one binding partner suitable for binding to the analyte sought and detecting and/or quantifying the latter, preferably specifically, even when said binding partner is not of immunological nature or origin in the strict sense.

Sandwich-type immunoassays (or more simply "sandwich immunoassays") use a first binding partner, termed "capture binding partner", to specifically bind the analyte sought, and a second binding partner, termed "detection binding partner" which is labeled and is also intended to specifically bind with the analyte sought, thus revealing the binding between the capture binding partner and the analyte, and thus the presence of the analyte. In other words, the analyte sought is taken "in a sandwich" between said first and second binding partners, the first ("capture") binding partner generally being present in excess relative to the analyte sought. The capture binding partner can, for example, be immobilized on a solid support (by covalent bonding, adsorption or any other appropriate method).

An epitope, also called antigenic determinant, is the smallest part of an antigen that can be recognized by a paratope which is the variable part of an antibody. The structure of the epitope is complementary to the paratope of the antibody. The structure involved may be the primary structure, in the case of a linear epitope, also called sequential epitope, or the tertiary structure in the case of a conformational epitope, also called discontinuous epitope.

The sequence of a linear epitope can comprise "conservative" modifications which do not significantly change the binding between the epitope and the antibody from a point of view of the specificity.

A mimotope is a macromolecule, often a peptide, which mimics the three-dimensional structure of a given epitope. An antibody which recognizes said epitope is also capable of recognizing and binding to the mimotope which mimics this epitope. In the case of antigens of protein nature, peptide mimotopes, which are thus linear, are often used to mimic conformational epitopes. According to the invention, the conformational epitopes can be replaced with mimotopes. The mimotopes are also included in the scope of the present application as a replacement for the term epitope.

When the antigen is of protein nature, as is often the case, the linear epitopes and the mimotopes correspond to a peptide sequence of variable length. In the case of linear epitopes, a distinction should be made between the notions of a minimal epitope and of an optimal epitope. The minimal epitope corresponds to the peptide sequence of the smallest size specifically recognized by the corresponding antibody. When an amino acid of the N-terminal end or of the C-terminal end of said peptide sequence is deleted, the binding of the antibody is no longer possible, and the recognition is lost. A minimum epitope can contain from 3 to 20 amino acids, more often from 4 to 8 amino acids.

The optimal epitope corresponds to the peptide sequence which is specifically recognized and has the best possible reactivity with respect to the corresponding antibody (the strongest signal). It very often involves peptide sequences of 6 to 30 amino acids in length. The optimal epitope as a general rule comprises the minimal epitope. In rare cases, the optimal epitope and the minimal epitope can be merged.

The compound of the invention is such that it contains two peptide sequences E1 and E2 comprising at least one epitope of an analyte. The expression "peptide sequence comprising at least one epitope of an analyte" is intended to mean that the peptide sequence consists at least of the amino acids of the minimal epitope. According to one embodiment of the invention, the peptide sequence consists of at most the amino acids of the optimal epitope. Of course, those skilled in the art know that it is also possible to add 1, 2, 3, 4 or 5 additional amino acids on one side of the optimal epitope or on both sides without having too great an effect on the antigenic recognition. Such additional amino acids are also included in the definition.

The amino acids of these peptide sequences may be the amino acids naturally found in the sequence of the analyte or else analogous amino acids. The term "analogous amino acids" is intended to mean two amino acids, the replacement of which is a conservative substitution that occurs in nature, that is to say that takes place in a family of amino acids. Specifically, amino acids are generally divided into 4 families, namely (1) acidic amino acids such as aspartate and glutamate, (2) basic amino acids such as lysine, arginine and histidine, (3) nonpolar amino acids such as alanine, leucine, isoleucine, proline, phenylalanine, methionine and tryptophan and (4) polar uncharged amino acids such as glycine, asparagine, glutamine, cysteine, serine, threonine and tyrosine. Phenylalanine, tryptophan and tyrosine are sometimes classified as aromatic amino acids. For example, it can reasonably be predicted that an isolated replacement of leucine with isoleucine or valine, of an aspartate with a glutamate, of a threonine with a serine, or a similar conservative replacement of an amino acid with another amino acid which is structurally related, will have no major effect on the biological activity or the antigenicity. Those skilled in the art will easily determine the amino acid that can tolerate a change with reference to the Hopp/Woods and Kyte-Doolite plots, well known in the art. According to one embodiment, the amino acids of the peptide sequence are the amino acids naturally found in the analyte. According to another embodiment, the peptide sequence E1 or the peptide sequence E2 or else both are mimotopes and consequently the amino acids of the peptide sequence are predominantly different than the amino acids naturally found in the analyte.

The term "analyte" denotes a substance of biological origin, contained in a sample, detected, identified and/or quantified by an analysis. It should be understood, in the broad sense, as denoting a chemical, biological or biochemical substance which is the subject of one or more analyses. By way of example of analytes, mention may be made of a protein or a peptide.

The analyte will be representative of a pathological condition or of the presence of a microorganism in a medium. The term "pathological condition" is intended to mean any impaired state of health of a patient, due to diseases caused by numerous factors, such as environmental (infectious), genetic and/or biological factors. By way of examples of diseases, mention may be made of infectious diseases, due to microorganisms such as viruses, bacteria or parasites (hepatitis, sepsis, etc.), autoimmune diseases, neurodegenerative diseases, cancers (breast, prostate, colon, etc.), cardiovascular diseases (myocardial infarction, etc.), etc. The analytes are then associated with the various diseases. By way of example of an analyte, mention may be made of cardiac troponin I which is of use as an analyte for myocardial infarction and prodefensin-A6 as a colon cancer analyte. These analytes will subsequently be described in greater detail. According to one embodiment, E1 and E2 are peptide sequences comprising at least one cardiac troponin I epitope or prodefensin-A6 epitope.

The central radical Z is an amino acid derivative bearing a thiol function before the bonding thereof with the carrier molecule. The term "amino acid derivative" is intended to mean any molecule forming two peptide bonds —CO—NH— with the linker arms X and Y to which it is bonded. To do this, the corresponding amino acid comprises, before the bonding thereof with the linker arms X or Y, a reactive group $—NH_2$ and a reactive group —COOH. After bonding to the linker arms X and Y, the amino acid derivative thus comprises a group —NH— and a group —CO—. The corresponding amino acid also comprises a thiol function (—SH) before the bonding thereof with the carrier molecule. Examples of such radicals Z comprise cysteine derivatives, homocysteine derivatives and penicillamine derivatives. The corresponding amino acids, used for forming these derivatives, are of course cysteine, homocysteine and penicillamine, which are amino acids known to those skilled in the art.

The two linker arms X and Y of the compound of the invention are identical to or different than one another. The linker arms are characterized by their capacity to each form two peptide bonds —CO—NH—, on the one hand with E1 or E2 and, on the other hand, with the central radical Z. The linker arms X and Y are then amino acid derivatives comprising a group —NH— and a group —CO—. To do this, the compounds used for forming the linker arms comprise, before the bonding thereof with the peptide sequences E1 or E2, a reactive group $—NH_2$ and a reactive group —COOH. Of course, the linker arms can comprise other groups, for example side groups, which are not reactive as such or are not reactive since they are protected by protective groups known to those skilled in the art, for example trityl, t-butyl, t-butyl ether benzyl or benzyl ester groups. The linker arms can be obtained from one or more compounds which each have a reactive group —COOH and a reactive group —NH$_2$ before they are involved in the bi-epitope compound of the invention. These compounds will be referred to as "monomers of use for forming the linker arms".

The monomers of use for forming the linker arms can be proteinogenic α-amino acids, required for the synthesis of biological proteins, which are known to those skilled in the art. These proteinogenic α-amino acids can be genetically coded; in this case, there are 22 of them. The 20 proteinogenic α-amino acids universally distributed in all living beings are: L-alanine, L-arginine, L-asparagine, L-aspartate, L-cysteine, L-glutamate, L-glutamine, L-glycine, L-histidine, L-isoleucine, L-leucine, L-lysine, L-methionine, L-phenylalanine, L-proline, L-serine, L-threonine, L-tryptophan, L-tyrosine and L-valine. The other 2 proteinogenic amino acids are much rarer: L-pyrrolysine is found only in some methanogenic archaea and L-selenocysteine is present only in some enzymes of the oxidoreductase family.

In addition to these 22 genetically coded amino acids, there are several tens of other biological amino acids that can be obtained from the above by enzymatic modifications, for instance L-citrulline, L-pyroglutamic acid, L-ornithine, L-3, 4-dihydroxyphenylalanine, γ-aminobutyric acid and domoic acid.

The monomers that are of use for forming the linker arms can also be pseudo amino acids, also known as artificial amino acids, that is to say non-biological amino acids. In this case, the only requirement is that the compound comprises two free functions, —COOH and —NH$_2$.

According to one particular embodiment of the invention, the linker arms and Y, which may be identical or different, each comprise one or more amino acid derivatives (such as proteinogenic α-amino acids, and/or biological amino acids and/or pseudo amino acids). The linker arms can be prepared from one to six amino acids, preferably from one to four amino acids. For example, the linker arms have the sequence GGGS (SEQ ID NO: 25), or the sequence SGGG (SEQ ID NO: 26), the sequence GSGSGS (SEQ ID NO: 27) or else the sequence SGSGSG (SEQ ID NO: 28).

According to one embodiment of the invention, X and Y in formula (I), that is to say after formation of the peptide bonds with E1/E2/Z, exhibit one or more derivatives of monomers of formula (II) below:

—NH—R—CO— (II)

in which R is a radical consisting of one or more groups chosen independently from the groups (—C(R')H—C(R")H, (—C(R')H—C(R")H—O—), (—C(R')H—) and (—C(R') H—O—), R' and R" being chosen independently from hydrogen, a hydroxyl group and $C_1$-$C_5$ alkyl groups. According to one embodiment, R consists of one or more groups chosen independently from (—CH$_2$—CH$_2$—O—), (—CH$_2$—O—) and (—CH$_2$—). According to one particular embodiment, the radical R may comprise from one to six groups (—CH$_2$—CH$_2$—O—), preferably from one to four groups (—CH$_2$—CH$_2$—O—). By way of nonlimiting examples of a radical R, mention may be made of pentaoxaoctadecanoyl, tetraoxapentadecanoyl, trioxadodecanoyl, trioxatridecanoyl, dioxaoctanoyl, oxapentoyl and hexaoxaheneicosanoyl and derivatives thereof. By way of example of a compound that is of use for giving a monomer derivative of formula (II), mention may be made of 8-amino-3,6-dioxaoctanoic acid (CAS No.: 134978-97-5), which is a known pseudo amino acid. For example, the linker arm may be a dimer or a trimer of 8-amino-3,6-dioxaoctanoic acid, $(Ado)_2$ or $(Ado)_3$.

By way of other example of groups of the radical R, mention may be made of the biological amino acid derivatives mentioned above, in residue form, that is to say without their —COOH and —NH$_2$ group but comprising an —NH— group and a —CO— group. Thus for example, if the compound forming the linker arm is leucine, of formula $(CH_3)_2CH$—$CH_2$—$CH(NH_2)$—COOH, then R of the compound of formula (II) will be

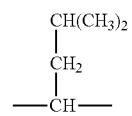

Each linker arm has, between the —CO and —NH groups of the two ends, a size of between 10 and 60 Å, preferably between 20 and 30 Å, which constitutes one particular embodiment of the invention.

Since the monomers that are of use for forming the linker arms X and Y have reactive groups —COOH and —NH$_2$ before they are involved in the bi-epitope compound of the invention and which allow the formation of peptide bonds, the sequence E1-X-Z-Y-E2 can be considered to be a peptide, hereinafter referred to as bi-epitope peptide, such that it can be produced by peptide synthesis, which has the advantages of
    easy, rapid standardized, reproducible and simplified synthesis,
    the production of a compound which is equimolar with respect to E1 and E2.

The bi-epitope peptide is obtained according to the procedures well known to those skilled in the art, such as the solid-phase peptide synthesis described by Merrifield, 1963. The improvements to this technique have been reviewed and discussed by Fields and Noble, 1990. Such a synthesis uses a solid phase to which the first C-terminal amino acid is attached, In this context, each —NH$_2$ group of the new amino acid, added so as to form the peptide, is protected with a protective group of Fmoc (9-fluorenylmethyloxycarbonyl) or Boc (t-butoxycarbonyl) type, in order to promote the reaction between the —NH$_2$ group presented by the solid phase and the —COOH group of the new amino acid added, as is well known to those skilled in the art.

According to the invention, the length of the bi-epitope peptide does not exceed a length corresponding to 100 amino acids, preferably it does not exceed a length corresponding to 20 to 30 amino acids and more preferentially it does not exceed a length corresponding to 25 to 27 amino acids.

The bi-epitope peptide is bonded, via the radical Z, to a carrier molecule. The carrier molecule has the role of stabilizing the bi-epitope compound and makes it possible to make the peptide sequences E1 and E2, comprising at least one epitope of the analyte of said bi-epitope compound, more available, this being while at the same time preserving equimolarity between E1 and E2.

The term "carrier molecule" is intended to mean any soluble molecule which can be coupled to a peptide. By way of soluble molecule, mention may be made of proteins such as bovine serum albumin, immunoglobulin G and thyroglobulin, and polymers such as polylysines. According to one embodiment, the carrier molecule is a protein of which the molecular weight is between 20 kDa and 700 kDa, preferably between 60 kDa and 250 kDa.

Polylysines are polymers known to those skilled in the art. They are available for example from Sigma-Aldrich.

Bovine serum albumin and thyroglobulin are known to those skilled in the art. For the immunoglobulin G, it should be chosen such that it comes neither from the species used to obtain the antibodies of the immunoassay, nor from the species from which the sample to be analyzed comes, in order to avoid interference problems. By way of example, mention may be made of rabbit, mouse, horse, goat, pig, etc., immunoglobulins G (non-exhaustive list).

According to one embodiment, the carrier molecule is bovine serum albumin.

According to another embodiment, the carrier molecule is a rabbit immunoglobulin G in an immunoassay in which the antibodies come from mice and in which the sample to be analyzed comes from human beings.

The coupling between the bi-epitope peptide and the carrier molecule of protein nature at the level of the radical Z can take place by covalence, according to methods well known to those skilled in the art. The sulfhydril group (—SH) present in the side chain of the radical Z is reactive with respect to maleimide, haloacetyl and pyridyl disulfide groups. Thus, in a first step, the carrier molecule should be activated by reaction with a molar excess of a crosslinker which will be capable of reacting at the level of the accessible amine groups (—$NH_2$) of the carrier molecule and of thus introducing, at the surface of the carrier molecule, reactive groups chosen from maleimides or haloacetyls. These groups are preferred because they make it possible to obtain coupling via a thioether bond which is stable. Among the crosslinkers which make it possible to introduce maleimide groups, mention may be made, non-exhaustively, of N—(ε-maleimidocaproyloxy)succinimide ester, m-maleimidobenzoyl-N-hydroxysuccinimide ester, succinimidyl 4-(N-maleimidomethyl)cyclohexane-1-carboxylate or else sulfo-succinimidyl 4-(N-maleimidomethyl)cyclohexane-1-carboxylate. Among the crosslinkers which make it possible to introduce haloacetyl groups, mention may be made, non-exhaustively, of N-succinimidyl(4-iodoacetyl)aminobenzoate and sulfosuccinimidyl(4-iodoacetyl)aminobenzoate. The activated carrier molecule is then purified by desalting, for example by gel filtration chromatography, or else by dialysis, in order to remove the excess crosslinker and the by-products. Finally, the activated carrier molecule is placed in the presence of the bi-epitope peptide comprising the radical Z in relatively central position. The maleimide or haloacetyl groups react with the sulfhydryl group (—SH) of the radical Z of the bi-epitope peptide so as to form a stable covalent thioether bond. The reaction between the maleimide and sulfhydryl groups should be carried out under conditions close to neutral pH (pH 6.5 to 7.5) and should exclude foreign thiols, for example most of the reducing agents, from the composition of the reaction buffer in order to avoid competition for the coupling sites. The reaction between the haloacetyl and the sulfhydryl groups should be carried out at pH 7.2 to 9. In order to limit the generation of free iodine which is capable of reacting with tyrosine, histidine and tryptophan, it is preferable to carry out the reaction in the dark. Such processes, known to those skilled in the art, are described for example in "Chemistry of Protein Conjugation and Cross-linking" by Shan S. Wong, CRC Press Inc., Boca Raton, Fla., United States, 1991.

In order to promote the coupling of the bi-epitope peptide on the radical Z, if the linker arms X/Y and/or the peptide sequences E1/E2 contain amino acid derivatives bearing a thiol function, it is advisable to use, for the formation of said peptide, amino acid derivatives that are protected at the level of this thiol function with a protective group which is stable during the steps of synthesis of said peptide and also during the step of coupling with the carrier molecule. Thus, only the amino acid used to give the radical Z will bear a reactive thiol function. In order to avoid such a step of protecting the thiol functions of the arms X/Y and/or of the peptide sequences E1/E2, it is advisable for neither X, nor Y, nor E1 nor E2 to contain an amino acid derivative bearing a thiol function, this constituting one particular embodiment of the invention.

Amino acids protected at the level of their thiol function are available for example from Novabiochem®.

After coupling of the bi-epitope peptide with the carrier molecule, the thiol functions will be optionally deprotected according to techniques known to those skilled in the art. As protective group, mention may be made of the t-butylthio group which is easily removed in an aqueous medium (0.1M ammonium bicarbonate) in the presence of DTT (dithiothreitol). When only the coupling arms X/Y contain amino acid derivatives bearing a thiol function, such a deprotection will not be necessary and will not be advised. When the peptide sequences E1/E2 contain amino acid derivatives bearing a thiol function, such a deprotection will be necessary if this affects the epitope recognition.

It is also possible for the coupling arms and/or the peptide sequences to contain no amino acid derivative bearing a thiol function. Thus, the bi-epitope compound of the invention comprises one or more of the following characteristics:
the linker arm X does not comprise an amino acid derivative bearing a thiol function,
the linker arm Y does not comprise an amino acid derivative bearing a thiol function,
the peptide sequence E1 does not comprise an amino acid derivative bearing a thiol function, and
the peptide sequence E2 does not comprise an amino acid derivative bearing a thiol function.

According to one particular embodiment, the peptide sequences E1 and E2 comprise no amino acid derivative bearing a thiol function. According to yet another embodiment, none of the elements among X, Y, E1 and E2 comprises an amino acid derivative bearing a thiol function.

The compound of the invention, for implementation thereof in an immunoassay, can be contained in a composition, which comprises or contains said compound of formula (I) in solution in water, in a buffer or in a biological fluid, this constituting another subject of the invention.

A composition containing the bi-epitope compound of formula (I) in solution in water is a clear liquid solution obtained by complete dissolution of said compound and the major solvent of which is water, representing at least 50% by volume relative to the total volume of the solution. The amount of solvent depends of course on the analyte involved and will be easily determined by the person skilled in the art.

The compound of formula (I) can also be in solution in a buffer. The buffers to be used are widely known to those skilled in the art and depend on the analyte involved. By way of example of buffers, mention may be made of buffers such as the PBS, HEPES and Tris-HCl buffers.

When the composition contains a biological fluid, said fluid can correspond to the sample that it is desired to test. By way of examples, mention may be made of total blood or derivatives thereof, for example serum or plasma, urine, saliva and effusions.

The amount of compound of formula (I) in the composition of the invention depends on the analyte involved and on the corresponding measurement range. It will easily be determined by those skilled in the art. Thus, it can be about one pg/ml, one ng/ml or one µg/ml.

The same characteristics and preferences described previously, in particular with regard to the choice of E1, E2, X, Y, Z, carrier molecule and analyte, also apply to the compositions of the invention.

Of course, the compositions of the invention can comprise other compounds, such as salts, filler proteins such as BSA or synthetic polymers of dextran or polyethylene glycol type, or detergents, well known to those skilled in the art.

As previously indicated, the compounds and the compositions of the invention are particularly advantageous since they are easily synthesized, are stable at +2/8° C. and are soluble under the conditions of an immunoassay. Moreover, the compounds of the invention have, against all expectations, an immunoreactivity to the binding partners used in the immunoassay that is particularly high, that is to say that the binding partners recognize them particularly well, such that, if it is desired to use them as a control, standard and/or adjuster, they can be contained in the control, standard and adjuster solutions in a low amount, while at the same time being stable under the immunoassay conditions.

Thus, another subject of the invention relates to the use of such a bi-epitope compound or of such a composition containing this compound, as a control or standard or adjuster in an immunoassay.

The term "use as a control of the compound of formula (I) or the composition containing this compound" is intended to mean the use thereof for, inter alia, verifying that the immunoassay operates according to expectations (also called positive control) and that the detection of the analyte in the test sample is not falsely negative.

The expression "use as a standard of the compound of formula (I) or the composition containing this compound" is intended to mean the use thereof for establishing a standard range. The establishment of the standard range, which is a necessary step to be able to carry out a quantification of an analyte, is a step widely known to those skilled in the art as previously described. It consists in measuring the signal generated by increasing and known amounts or concentrations of the analyte, in plotting the curve giving the signal as a function of the amount or of the concentration and in finding a mathematical model which represents this relationship as reliably as possible. To do this, several aqueous compositions of the invention are used, each containing a different concentration of analyte. The mathematical model will be used to determine by extrapolation the unknown amounts or concentrations of analyte contained in the test sample.

The expression "use as an adjuster, also called calibrator, of the compound of formula (I) or the composition containing this compound, which is a particular standard" is intended to mean the use thereof for adjusting the measurement of the immunoassay of the analyte. In this case, the concentration of analyte is fixed and known. The signal generated during the use in the immunoassay by the adjuster is also known. The adjuster serves to verify that the measurement (signal) produced during the implementation of the immunoassay indeed corresponds to the expected value. If this is not the case, the adjuster serves to measure the derivation that it will be possible, where appropriate, to mathematically correct or to correct by physical intervention on the measuring instrument (adjustment). For convenience, the term "standard" will, in the present application, comprise the term "adjuster".

As previously indicated, the analyte is any substance of biological, chemical or biochemical origin contained in a sample, that is detected, identified and/or quantified by an analysis.

According to a first embodiment, the analyte is cardiac troponin I and the compound of formula (I) or a composition containing it is used as a control, standard or adjuster in a cardiac troponin I immunoassay.

It is known that troponin is a myofibrillar protein complex consisting of three proteins, troponins I, T and C. This protein complex makes it possible to contribute to the regulation of $Ca^{2+}$ ion-mediated muscle contraction, by interacting with myosin and actin.

Cardiac troponin I (Uniprot accession No. P19429) is the troponin subunit responsible for the inhibition of binding between myosin and actin.

Cardiac troponin I epitopes and mimotopes are known to those skilled in the art. In one particular mode of the invention, the peptide sequences E1 and E2 are chosen from the following sequences:

```
Sequence 1:
                                        (SEQ ID NO: 1)
ATEPHAKKK Sequence 2:
                                        (SEQ ID NO: 2)
AGLGFAELQDL Sequence 3:
                                        (SEQ ID NO: 3)
KISASRKLQLKT
```

The peptide sequences deriving from said peptide sequences by substitution, deletion or insertion of an amino acid also belong to the field of the invention, insofar as they retain the capacity to be recognized by the antibody in question.

According to another embodiment, the compound of formula (I) or a composition containing it is used as a control, standard or adjuster in a prodefensin-A6 immunoassay.

Defensins are a family of antimicrobial peptides involved in host defense against microbial attacks. In the mature form, they consist of 30 to 40 amino acids and have the property of selectively disaggregating membranes. Like other eukaryotic proteins, defensins can be present not only in mature protein form but also in precursor form. The term "prodefensin" is then used. Prodefensin-A6 (Uniprot accession No. Q01524) has been described as possibly being of use as a marker in the context of cancer and in particular of colorectal cancer, in particular in patent application WO 2010/112777 by the applicant.

Prodefensin-A6 protein epitopes and mimotopes are known and are described for example patent application WO 2010/112777. In one particular mode of the invention, the peptide sequences E1 and E2 are chosen independently from the following groups of sequences, given that, if E1 is chosen from one group, E2 is chosen from another group:

```
Group 1:
Sequence 4:
                                        (SEQ ID NO: 4)
NYVTPPWAIFRH Sequence 5:
                                        (SEQ ID NO: 5)
WTGVLSPTQEYR
```

-continued

Sequence 6:
SHLTPPWMDYRV (SEQ ID NO: 6)

Sequence 7:
VMAVTCSTCDSR (SEQ ID NO: 7)

Sequence 8:
LTPPTEDLRPPD (SEQ ID NO: 8)

Group 2:
Sequence 9:
YGNHSCTHIGHC (SEQ ID NO: 9)

Sequence 10:
GPSYTCLHFGHC (SEQ ID NO: 10)

Sequence 11:
TEREVHNWFPFH (SEQ ID NO: 11)

Group 3:
Sequence 12:
YPHPWSMHVIRA (SEQ ID NO: 12)

Sequence 13:
TTTPHPWALFAV (SEQ ID NO: 13)

Sequence 14:
TPHPWQRWVVYS (SEQ ID NO: 14)

Sequence 15:
EDVLRWHPEWPG (SEQ ID NO: 15)

Group 4:
Sequence 16:
YHETWPPKSAQL (SEQ ID NO: 16)

Sequence 17:
YHDNWPQPSRSW (SEQ ID NO: 17)

Sequence 18:
QHNHQRHGAMGA (SEQ ID NO: 18)

Sequence 19:
YHDMWPMSGRMA (SEQ ID NO: 19)

Sequence 20:
YHDNWPPLNGAR (SEQ ID NO: 20)

Sequence 21:
YHDMWPAIQLSP (SEQ ID NO: 21)

Sequence 22:
YHEKFPGPVVLP (SEQ ID NO: 22)

Group 5:
Sequence 23:
QAEDDPLQAK (SEQ ID NO: 23)

These controls, standards and/or adjusters are particularly suitable for use in processes for detecting and/or quantifying an analyte by immunoassay in a test sample that may contain said analyte.

Thus, another subject of the invention relates to a process for detecting an analyte by immunoassay in a test sample that may contain said analyte, comprising
 i. an immunoassay test by bringing said test sample into contact with one or more binding partners for the analyte,
 ii. a test to verify the validity of the immunoassay test by bringing a bi-epitope compound of formula I as previously defined or a composition as previously defined, by way of positive control, into contact with said one or more binding partners for the analyte,
 iii. the reading of the immunoassay test if the validity verification test is positive,
 iv. the determination of the presence of said analyte in the test sample when the signal obtained by the immunoassay test of step i is greater than the detection threshold of the immunoassay test.

The test sample in the context of the invention may be of various origins, for example of food, environmental, biological, veterinary, clinical, pharmaceutical or cosmetic origin.

Among the samples of food origin, mention may be made, nonexhaustively, of a sample of milk products (yoghurts, cheeses, etc.), of meat, of fish, of eggs, of fruit, of vegetables, of water, of beverages (milk, fruit juice, soda, etc.). Of course, these samples of food origin may also come from sauces or more elaborate dishes or non-transformed or partially transformed raw materials. A food sample may also be derived from an animal feed, such as oil cakes or animal meals. All these samples, if they are not liquid, are pretreated so as to be in liquid form.

As previously indicated, the sample may be of environmental origin and may consist, for example, of a surface sampling, a water sampling, etc.

The sample may also consist of a biological sample, of human or animal origin, which may correspond to samplings of biological fluid (urine, total blood or derivatives such as serum or plasma, saliva, pus, cerebrospinal fluid, etc.), of stools (for example choleraic diarrhea), nose, throat, skin, wound, organ, tissue or isolated cell samplings, or swab samples. This list is obviously not exhaustive.

Generally, the term "sample" refers to a portion or an amount, more particularly a small portion or a small amount, taken from one or more entities for analytical purposes. This sample can optionally have undergone a pretreatment, involving for example mixing, diluting or else milling steps, in particular if the starting entity is in the solid state.

The sample analyzed may generally contain, or is suspected of containing, at least one analyte representative of the presence of microorganisms or of a disease to be detected, characterized or monitored.

The steps of this process for detecting an analyte by immunoassay are steps widely known to those skilled in the art which have been previously described. In particular, the first step consists in bringing the test sample into contact with one or more binding partners for the analyte, preferably two binding partners for a sandwich test. As previously described, one of the two partners can be coupled to a label so as to form a conjugate or a tracer. The other binding partner can be captured on a solid support as is known to those skilled in the art. The term "capture partner" is then used for the latter and "detection partner" for the former.

The measured signal emitted by the conjugate is then proportional to the amount of analyte in the biological sample.

The binding partners for the analyte of interest are any molecule capable of binding to the analyte. By way of example of binding partners for the analyte, mention may be made of the binding partners of immunological nature or origin, such as (monoclonal or polyclonal) antibodies and antibody fragments, well known to those skilled in the art, and also binding partners which are not of immunological nature or origin, such as nanofitins, receptors for the analyte if they exist, aptamers, DARPins or any other molecule which is known to have an interaction with said analyte.

Nanofitins (tradename) are small proteins which, like antibodies, are capable of binding to a biological target, thus making it possible to detect it, to capture it or quite simply to target it within an organism.

Aptamers are oligonucleotides, generally RNA or DNA, identified in libraries containing up $10^{15}$ different sequences, by a combinatorial method of in vitro selection called SELEX for "Systematic Evolution of Ligands by Exponentiel Enrichment" (Ellington A D and Szostak J W., 1990). Most aptamers are RNA compounds, owing to the capacity of RNA to adopt varying complex structures, thereby making it possible to create, at its surface, cavities of various geometries, making it possible to bind various ligands. They are biochemical tools of interest that can be used in biotechnological, diagnostic or therapeutic applications. Their selectivity and their ligand-binding properties are comparable to those of antibodies.

"DARPins" for Designed Ankyrin Repeat ProteINS (Boersma Y L and Plütckthun A, 2011) are another class of proteins which make it possible to mimic antibodies and to be able to bind with high affinity and high selectivity to target proteins. They derive from the family of ankyrin proteins which are adaptor proteins that make it possible to bind the membrane proteins integral to the spectrin/actin network which constitutes the "vertebral column" of the cell plasma membrane. The structure of ankyrins is based on the repetition of a unit of approximately 33 amino acids and the same is true for DARPins. Each unit has a secondary structure of helix-turn-helix type. DARPins contain at least three, preferably four to five repeated units and are obtained by screening of combinatorial libraries.

The term "label" is intended to mean, in particular, any molecule containing a group that is reactive with a group of the binding partner, directly without chemical modification, or after chemical modification so as to include such a group, which molecule is capable of directly or indirectly generating a detectable signal. A nonlimiting list of these direct detection labels consists of:
- enzymes which produce a signal detectable for example by colorimetry, fluorescence or luminescence, such as horseradish peroxidase, alkaline phosphatase, beta-galactosidase or glucose-6-phosphate dehydrogenase,
- chromophores such as fluorescent, luminescent or dye compounds,
- radioactive molecules such as $^{32}P$, $^{35}S$ or $^{125}I$,
- fluorescent molecules such as Alexas or phycocyanines, and
- electrochemiluminescent salts such as organometallic derivatives based on acridinium or on ruthenium.

Indirect detection systems can also be used, for instance ligands capable of reacting with an anti-ligand. The ligand then corresponds to the label for constituting, with the binding partner, the conjugate.

Ligand/anti-ligand pairs are well known to those skilled in the art, which is the case for example with the following pairs: biotin/streptavidin, hapten/antibody, antigen/antibody, peptide/antibody, sugar/lectin, polynucleotide/polynucleotide complementary thereto.

The anti-ligand may then be directly detectable by the direct detection labels previously described or may itself be detectable by another ligand/anti-ligand pair, and so on.

These indirect detection systems can result, under certain conditions, in an amplification of the signal. This signal amplification technique is well known to those skilled in the art, and reference may be made to the prior patent applications FR 2781802 or WO 95/08000 by the applicant.

Depending on the type of labeling used, those skilled in the art will add reagents which enable the visualization of the labeling or the emission of a signal detectable by any type of appropriate measuring device, for instance a spectrophotometer, a spectrofluorimeter, a densitometer or else a high-definition camera.

The step which is the test to verify the validity of the immunoassay is as described previously.

The immunoassay test i) and the verification test ii) can be carried out in any order, simultaneously or successively, optionally on the same solid support.

The reading of the immunoassay test is also a step widely known to those skilled in the art which depends on the test used.

Finally, the last step consists of the determination of the presence of said analyte in the test sample when the signal obtained by the immunoassay test of step i is greater than the detection threshold of the immunoassay test. This step is also widely known to those skilled in the art.

In addition to the detection, the compounds of the invention are also suitable for the quantification of an analyte in a test sample. Thus, another subject of the invention relates to a process for quantifying an analyte by immunoassay in a test sample that may contain said analyte, comprising
  i. an immunoassay test by bringing said test sample into contact with one or more binding partners for the analyte,
  ii. a test to verify the validity of the immunoassay test by bringing a positive control into contact with said one or more binding partners for the analyte,
  iii. the reading of the immunoassay test if the validity verification test is positive, and
  iv. the determination of the amount of said analyte in the test sample by comparison of the signal of the immunoassay test with a standard curve obtained beforehand, using a bi-epitope compound of formula (I) as previously defined or a composition as previously defined.

Said steps of the quantification process are as previously defined. In particular, the immunoassay test i) and the verification test ii) can be carried out in any order, simultaneously or successively, optionally on the same solid support.

In this quantification process, the positive control may be any compound that is of use as a control, which has an antigenic reactivity comparable to the analyte in the immunoassay used. According to one embodiment, the positive control is a bi-epitope compound or a composition as previously defined.

The standard curve is prepared with the compound or the composition of the invention. Nevertheless, any other appropriate standard solution can be used. Thus, another subject of the invention relates to a process for quantifying an analyte by immunoassay in a test sample that may contain said analyte, comprising
  i. an immunoassay test by bringing said test sample into contact with one or more binding partners for the analyte,
  ii. a test to verify the validity of the immunoassay test by bringing a bi-epitope compound of formula I as previously defined or a composition as previously defined, as a positive control, into contact with said one or more binding partners for the analyte, iii. the reading of the immunoassay test if the validity verification test is positive, and iv. the determination of the amount of said analyte in the test sample by comparison of the signal of the immunoassay test with a standard curve.

The same characteristics and preferences previously described, in particular with regard to the choice of the particular compounds and of the analytes, to the various steps of the immunoassay, also apply to the detection and quantification processes of the invention.

In particular, in all these detection and quantification processes, the analyte may be cardiac troponin I or prodefensin-A6.

The immunoassay processes of the invention involve the use of diagnostic kits comprising the compounds or compositions of the invention, this constituting another subject of the invention.

In addition to the compounds or compositions of the invention as described above, the kits according to the invention can also contain the compounds required for the implementation of a process for detecting or quantifying by immunoassay the presence of an analyte of interest, for example by sandwich-type immunoassay, such as the binding partners and all the compounds required for demonstrating the reaction between the binding partner(s) and the analyte of interest.

BRIEF DESCRIPTION OF THE FIGURES

The invention will be understood more clearly by means of the following examples which are given by way of nonlimiting illustration, and also by means of the figures, in which.

EXAMPLES

Example 1: Peptide Synthesis

Figure 1:
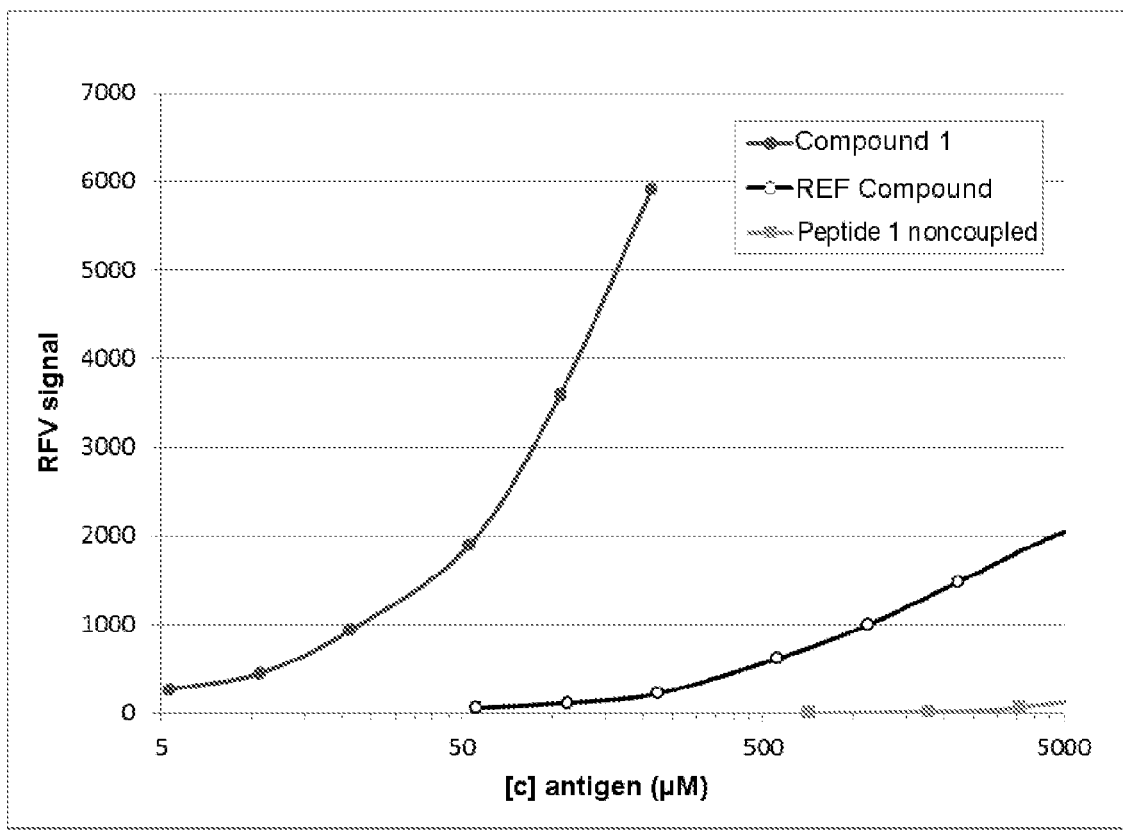
FIG. 1 is a graph giving the fluorescence signal RFV, determined by the VIDAS® automated device, emitted by a bi-epitope compound according to the prior art (REF Compound), a bi-epitope compound according to the invention (Compound 1) and a bi-epitope peptide corresponding to the bi-epitope compound 1 of the invention, but not coupled to a carrier molecule (noncoupled Peptide 1), as a function of their concentration.

The peptide syntheses were carried out using either the ABI 433A synthesizer from Applied Biosystems (Foster City, Calif., United States), or the Liberty synthesizer from CEM Corporation (Matthews, N.C., United States). The Rink Amide MBHA resin (Cat. No. 855003, Novabiochem®, Merck Millipore, Molsheim, France) was used as polymeric solid support.

At the end of the chemical synthesis, the peptides were deprotected and cleaved from the polymer in the presence of a mixture of trifluoroacetic acid-ethanedithiol-triisopropylsilane-water (94/2.5/1/2.5 V/V/V/V) for approximately 2 hours. After elimination of the polymer by filtration, the peptides were isolated by precipitation from diethyl ether at 0° C.

In order to increase their degree of purity, the peptides were purified by reverse-phase preparative high performance liquid chromatography (HPLC) on a Vynac Denali™ 120 Å C18, 10 µm column (Mandel Scientific Company Inc., Guelph, Ontario, Canada). Each peptide was eluted with a stepwise gradient of acetonitrile (from 0 to 95%) in aqueous solution containing 0.1% of trifluoroacetic acid, the percentage of acetonitrile of the steps having been chosen so as to optimize the isolation of the peak which corresponds to the peptide of interest. After this final step, two different analysis techniques were carried out in order to verify and characterize the peptides obtained.

For each peptide, an analytical HPLC profile was generated on a Chromolith® High Resolution RP-18 encapped reverse-phase column (Merck Millipore, Molsheim, France). The elution was carried out by means of a linear gradient of acetonitrile (from 0 to 100%) in aqueous solution containing 0.1% of trifluoroacetic acid and monitored by measuring the absorbance at 214 nm. This analysis makes it possible to determine the level of purity of the peptide.

Each peptide was also analyzed by liquid chromatography-mass spectrometry (LC/MS) on a Zorbax Eclipse Plus C18 RRHD 2.1×50 mm column, particle size 1.8 µm (Agilent Technologies, Santa Clara, Calif., United States) coupled to an Accurate-Mass Q-TOF LC/MS 6540UHD mass spectrometer (Agilent Technologies). This analysis makes it possible to determine the molar mass of the peptide.

The sequences of the peptides synthesized and also the characterization results are presented in Table 1.

TABLE 1

Sequences and characteristics of the peptides synthesized.

| Identifier | Analyte | Sequence | Amount obtained (mg) | Purity | Molar mass measured (Daltons) |
|---|---|---|---|---|---|
| Peptide 1 | TnI | ATEPHAKKK-Ado$_2$-C-Ado$_2$-AGLGFAELQDL-NH$_2$ (SEQ ID NOS: 1 and 2) | 78.8 | 97% | 2806.47 |
| Peptide 2 | TnI | ATEPHAKKKC-NH$_2$ (SEQ ID NO: 29) | 48.0 | 97% | 1110.60 |

TABLE 1-continued

Sequences and characteristics of the peptides synthesized.

| Identifier | Analyte | Sequence | Amount obtained (mg) | Purity | Molar mass measured (Daltons) |
|---|---|---|---|---|---|
| Peptide 3 | TnI | AGLGFAELQDLC-NH$_2$ (SEQ ID NO: 30) | 50.0 | 95% | 1234.60 |
| Peptide 4 | TnI | KISASRKLQLKT-Ado$_2$-C-Ado$_2$-AGLGFAELQDL-NH$_2$ (SEQ ID NOS: 2 and 3) | 59.7 | 99% | 3169.75 |
| Peptide 5 | TnI | ATEPHAKKKGGGSCSGGG AGLGFAELQDL-NH$_2$ (SEQ ID NO: 24) | 10.0 | 89% | 2741.36 |
| Peptide 6 | PDEF-A6 | QAEDDPLQAK-Ado$_2$-C-Ado$_2$-WTGVLSPTQEYR-NH$_2$ (SEQ ID NOS: 5 and 23) | 32.0 | 99% | 3215.50 |

The abbreviation TnI corresponds to cardiac troponin I and PDEF-A6 to prodefensin-A6. The abbreviation Ado corresponds to 8-amino-3,6-dioxaoctanoic acid (CAS No.: 134978-97-5).

The procedure for the couplings is the following:
Firstly, the protein chosen as carrier molecule was activated in the presence of an excess of Sulfo-SMCC (sulfo-succinimidyl-4-(N-maleimidomethyl)cyclohexane-1-car-

TABLE 2

Summary of the bi-epitope compounds according to the invention obtained (formula I) and tested in terms of immunoreactivity

| Identifier | Analyte | Epitope E1 | Epitope E2 | Arm X | Arm Y | Carrier molecule |
|---|---|---|---|---|---|---|
| Compound 1 | TnI | ATEPHAKKK (SEQ ID NO: 1) | AGLGFAELQDL (SEQ ID NO: 2) | (Ado)$_2$ | (Ado)$_2$ | BSA |
| Compound 2 | TnI | KISASRKLQLKT (SEQ ID NO: 3) | AGLGFAELQDL (SEQ ID NO: 2) | (Ado)$_2$ | (Ado)$_2$ | BSA |
| Compound 3 | TnI | ATEPHAKKK (SEQ ID NO: 1) | AGLGFAELQDL (SEQ ID NO: 2) | (Ado)$_2$ | (Ado)$_2$ | IgG |
| Compound 4 | TnI | ATEPHAKKK (SEQ ID NO: 1) | AGLGFAELQDL (SEQ ID NO: 2) | GGGS (SEQ ID NO: 25) | SGGG (SEQ ID NO: 26) | BSA |
| Compound 5 | PDEF-A6 | QAEDDPLQAK (SEQ ID NO: 23) | WTGVLSPTQEYR (SEQ ID NO: 5) | (Ado)$_2$ | (Ado)$_2$ | BSA |

The abbreviation TnI corresponds to cardiac troponin 1 and PDEFA6 to prodefensin-A6. The abbreviation Ado corresponds to 8-amino-3,6-dioxaoctanoic acid (CAS No.: 134978-97-5). The abbreviation BSA corresponds to bovine serum albumin. The IgG is rabbit immunoglobulin G.

Example 2: Preparation of the Bi-Epitope Compounds

The bi-epitope compounds were obtained by carrying out covalent couplings between, on the one hand, the peptides obtained in Example 1 and, on the other hand, carrier molecules. Table 2 presents in detail the various bi-epitope compounds according to the invention that were prepared. All these compounds correspond to formula I. Table 3, for its part, summarizes all of the couplings performed, while specifying the peptide and carrier-molecular pairs.

boxylate, CAS No.: 92921-24-9, Cat. No. 22322, Pierce, Thermo Scientific, Villebon sur Yvette, France). For the bovine serum albumin (BSA, Proliant Health & Biologicals, Ankeny, Iowa, United States), a 1/20 BSA/SMCC molar ratio was chosen. Thus, the BSA was diluted to 10 mg/ml in PBS (phosphate buffered saline), pH 7.2, and 53 μl of a solution of sulfo-SMCC at 25 mg/ml in water, prepared extemporaneously, was added dropwise. After incubation for 1 hour±5 minutes at 30° C.±2° C. in a water bath, with gentle magnetic stirring, the BSA-SMCC was dialyzed against a 50 mM phosphate buffer containing 150 mM NaCl, pH 6.8, in dialysis tubing having a cut-off threshold of 12 to 14 kDa. The dialysis was performed at ambient temperature and the dialysis bath was changed every hour, 3 times. After the dialysis, the protein concentration of the BSA-SMCC solution was determined by measuring the absorbance at 280 nm and this concentration was adjusted to 5 mg/ml in 50 mM phosphate buffer containing 150 mM NaCl, pH 6.8. This step makes it possible to modify the surface of the carrier molecule which from then on bears several reactive groups of maleimide type.

The peptide to be coupled was dissolved at 5 mg/ml in 50 mM phosphate buffer containing 150 mM NaCl and 5 mM EDTA, pH 6.8, taking into account the purity. A 1/10 BSA/peptide molar ratio was chosen. Thus, 2.35 mg of BSA-SMCC at a concentration of 5 mg/ml (0.47 ml) were added to 1 mg of peptide at a concentration of 5 mg/ml (200 μl). This mixture was incubated for a minimum of 16 hours at 2/8° C. on a wheel. The reaction was then blocked by adding 0.1 M of 2-mercaptoethylamine (CAS No. 60-23-1, cysteamine) in 50 mM phosphate buffer containing 150 mM NaCl, pH 6.8, prepared extemporaneously. After incubation for 20±5 minutes on a wheel at the laboratory temperature, the peptide-BSA conjugate was dialyzed against a PBS buffer, pH 7.2, in dialysis tubing having a cut-off threshold of 12 to 14 kDa. The dialysis was continued for a minimum of 16 hours at 2/8° C. After the dialysis, the protein concentration was adjusted to a theoretical concentration of 2 mg/ml of BSA in PBS buffer, pH 7.2. The concentration of the peptide-BSA conjugate was then determined by measuring the absorbance at 280 nm. This step allows the reaction between the maleimide groups and the sulfhydril groups (—SH) of the peptide, at the level of the terminal or median cysteine depending on the peptide sequence to be coupled, in order to form thioether bonds.

The compounds 1, 2, 4 and 5 were all obtained by applying the procedure described above. For the REF compound, which corresponds to the bi-epitope compound as described in patent U.S. Pat. No. 6,114,180, the same procedure was also applied, except that 2 peptides (peptide 2 and peptide 3) were placed in the presence of BSA-SMCC simultaneously and each peptide was coupled at a theoretical BSA/peptide molar ratio of 1/10. For the compound 3, peptide 1 was coupled to the rabbit polyclonal immunoglobulin G (bioMérieux). The procedure was identical, except that the BSA was replaced with another carrier molecule. The theoretical carrier molecule/peptide molar ratio was 1/10.

TABLE 3

Summary of the peptide-carrier molecule couplings

|  | Identifier | Peptide | Carrier molecule |
|---|---|---|---|
| Bi-epitope compounds according to the invention | Compound 1 | Peptide 1 | BSA (bovine serum albumin) |
|  | Compound 2 | Peptide 4 | BSA |
|  | Compound 3 | Peptide 1 | Rabbit immunoglobulin G |
|  | Compound 4 | Peptide 5 | BSA |
|  | Compound 5 | Peptide 6 | BSA |
| Bi-epitope compound according to the prior art (U.S. Pat. No. 6,114,180) | REF compound | Peptide 2 and Peptide 3 | BSA |

Example 3: Study of the Immunoreactivity of the Bi-Epitope Compound 1 According to the Invention The study of the bi-epitope nature of the compounds was carried out by means of a cardiac troponin I immunoassay using the VIDAS® immunoanalysis automated device (bio-Mérieux). The single-use tip serves both as solid phase for the reaction and as pipetting system. The cartridge is composed of 10 wells (X0 to X9) covered with a sealed and labeled sheet of aluminum. The first well (X0) comprises a precut part so as to facilitate the introduction of the sample. The last well (X9) is an optical cuvette in which the fluorescence of the substrate is measured. The various reagents required for the analysis are contained in the intermediate wells. All the steps of the test are carried out automatically by the instrument. They consist of a succession of cycles of suctioning/blowing back of the reaction medium. The cardiac troponin I immunoassay was carried out by means of a single-step sandwich test.

a) Sensitization and Passivation of the Tips

The characteristics and the suppliers of the antibodies used are presented in Table 4. The tips were sensitized with 300 μl of a solution of the 19C7 and B90 monoclonal antibodies each diluted to 2.5 μg/ml in a PBS buffer, pH 6.2. After approximately 20 h of incubation at +18/25° C. with the sensitizing solution, the tips were emptied. 300 μl of this same solution containing 10 g/l of bovine serum albumin are then added. The passivation continues at +18/25° C. overnight. The tips are emptied, dried, and then stored at +4° C. until use, in a moisture-free environment.

TABLE 4

Antibodies used for the cardiac troponin I immunoassay

| Antibody name | Target | Sequence of E1 or E2 | Supplier (Cat. No.) |
|---|---|---|---|
| 19C7 | TnI | KISASRKLQLKT (SEQ ID NO: 3) | Hytest (4T21-19C7) |
| B90 | TnI | ATEPHAKKK (SEQ ID NO: 1) | SDIX (B9085MA06-MA) |
| 3D5F7 | TnI | AGLGFAELQDL (SEQ ID NO: 2) | bioMérieux (noncommercial) |
| 7B9 | TnC | NA | Hytest (4T27-7B9) |

NA: not available.
The abbreviation TnI corresponds to cardiac troponin I and the abbreviation TnC corresponds to cardiac troponin C. The abbreviation Cat. No. corresponds to the catalog reference of the supplier.

b) Immunoassay Procedure

The test compounds were diluted in a PBS-BSA buffer at various concentrations and assayed as sample.

As soon as the VIDAS® tip is in contact with the sample, the immunological reaction begins because the capture antibodies are immobilized on this tip. The automated device mixes the test sample (135 μl) with 270 μl of the solution of conjugate. This solution contains the 2 monoclonal antibodies, 3D5F7 and 7B9, in the form of Fab' fragments coupled to alkaline phosphatase. These conjugates were diluted to approximately 0.75 μg/ml in a 100 mM phosphate buffer, pH 6.4, also containing 150 mM of NaCl and filler proteins.

The incubation lasts 6.8 minutes at 37° C. and enables the specific binding of the cardiac troponin I, or of the cardiac TnI bi-epitope compounds, or the cardiac TnI peptides, on the one hand to the antibodies adsorbed onto the tip and, on the other hand, to the conjugates. The unbound components are then removed by 3 washes with a 200 mM Tris buffer, pH 7.8, containing 300 mM NaCl and 0.2% Triton X-100. During the final revealing step, the 4-methylumbelliferyl phosphate substrate is suctioned up and then blown back in the tip; the enzyme of the conjugate catalyzes the reaction for hydrolysis of this substrate to 4-methylumbelliferone, the emitted fluorescence of which is measured at 450 nm. The value of the fluorescence signal (RFV=relative fluorescence value) is proportional to the concentration of the antigen present in the sample.

Table 5 summarizes the fluorescence signals (RFV=relative fluorescence value) determined by the VIDAS® automated device when the immunoreactivity of the REF bi-epitope compound (prior art), of the bi-epitope compound 1 according to the invention and of the non-coupled peptide 1 (Example 1) is compared. FIG. 1 represents these same data in graph form. As a reminder, peptide 1 comprises 2 cardiac TnI epitopes, one recognized by the B90 capture antibody of the immunoassay previously described, and the other by the 3D5F7 detection antibody. In compound 1 according to the invention, peptide 1 is coupled via the median cysteine on BSA in order to ensure better antigen presentation thereof and improved stability. The REF compound has the same two TnI epitopes also coupled to BSA. Unlike compound 1, each of the 2 epitopes is in the form of an individual peptide (peptides 2 and 3) which has been coupled to BSA at the level of the terminal cysteine. Compound 1, the REF compound, which corresponds to a bi-epitope compound as described in patent U.S. Pat. No. 6,114,180, and peptide 1, which corresponds to a synthetic bi-epitope compound as described in patent application WO 98/24816, are both reactive in the cardiac TnI immunoassay, but their levels of reactivity are very different. Thus, in order to obtain a signal of approximately 1000 RFV, 21 µM of compound 1 are necessary compared with 1118 µM of the REF compound, that is to say approximately 50 times less. Compound 1 thus exhibits much better immunoreactivity than the REF compound. Moreover, the good dynamics of the VIDAS® signal obtained with Compound 1 is not reproduced with the REF compound, even when testing much higher concentrations of this compound. The non-coupled peptide 1 is much less well recognized than the two bi-epitope compounds coupled to BSA.

Figure 2:
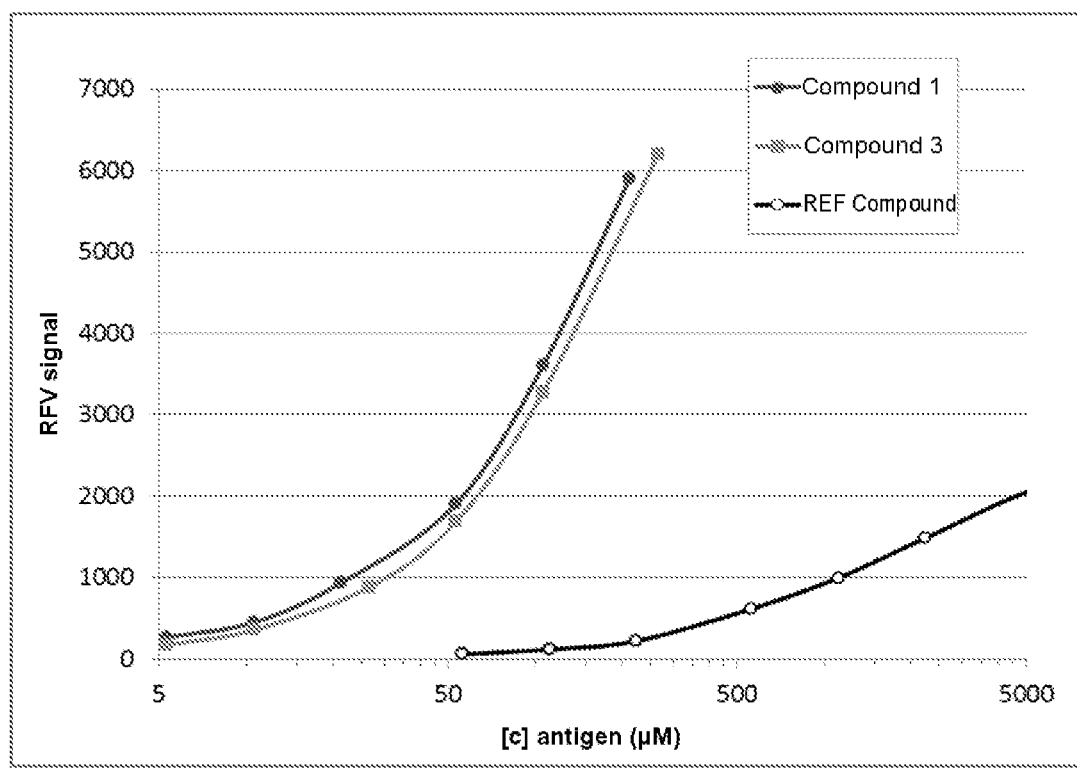
FIG. 2 is a graph giving the fluorescence signal RFV, determined by the VIDAS® automated device, emitted by the bi-epitope compound according to the prior art (REF Compound) and bi-epitope compounds according to the invention (Compounds 1 and 3), as a function of their concentration.

Example 4: Comparison of the Immunoreactivity of the Bi-Epitope Compounds According to the Invention Using Various Carrier Molecules In this example, peptide 1 which comprises 2 different epitopes of cardiac TnI was coupled to 2 different carrier molecules: BSA (compound 1) and rabbit immunoglobulin G (compound 3). The obtaining of these bi-epitope compounds is described in Example 2. The comparison of the immunoreactivity of these compounds in the cardiac TnI immunoassay was carried out as described in Example 3 and the results are presented in Tableau 5 above and FIG. 2, which represents a graph giving the RFV fluorescence signals emitted by the various compounds, bi-epitope compound according to the prior art (REF Compound) and bi-epitope compounds according to the invention (Compounds 1 and 3), as a function of their concentration. The results show that compounds 1 and 3 are both reactive in the cardiac TnI immunoassay and exhibit a comparable reactivity which is much greater than that observed for the REF compound.

Figure 3:
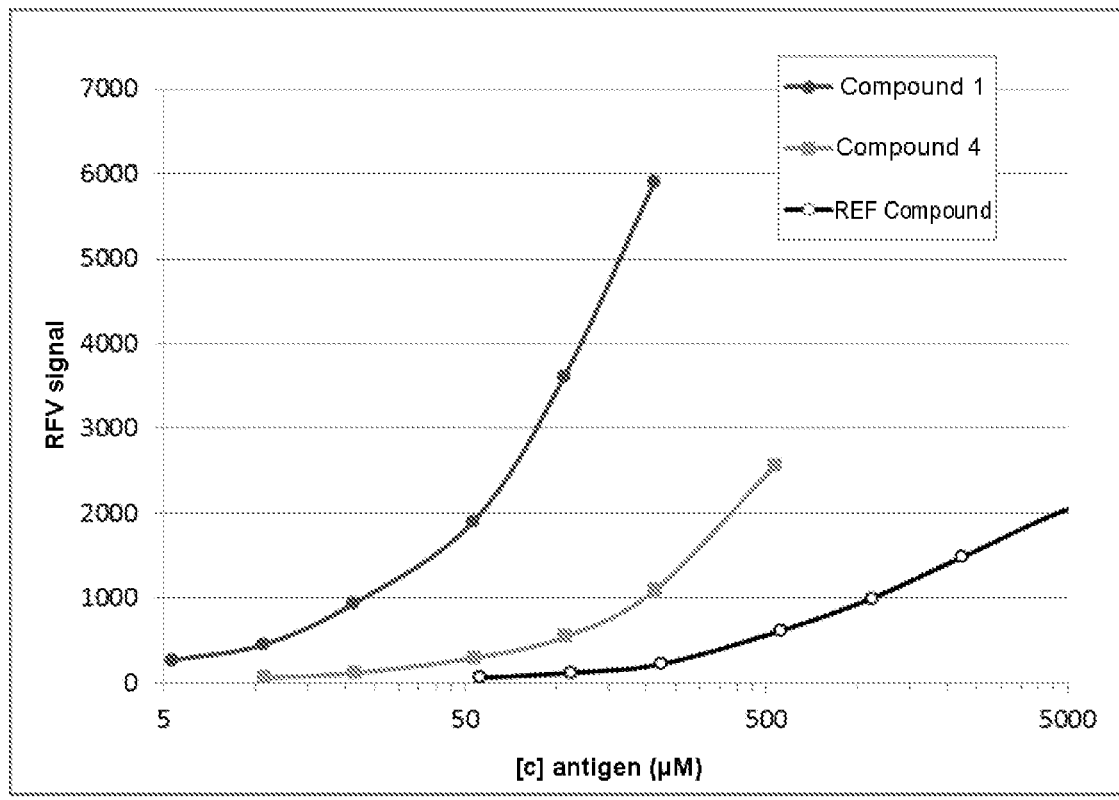
FIG. 3 is a graph giving the fluorescence signal RFV, determined by the VIDAS® automated device, emitted by the bi-epitope compound according to the prior art (REF Compound) and bi-epitope compounds according to the invention (Compounds 1 and 4), as a function of their concentration.

Example 5: Comparison of the Immunoreactivity of the Bi-Epitope Compounds According to the Invention Using Various Spacer Arms In this example, the bi-epitope compounds compared differ only in terms of the spacer arm. In the case of compound 1, the two spacer arms are identical, it is a dimer of the Ado artificial amino acid. Compound 4, for its part, comprises the GGGS sequence as arm X and the SGGG sequence as arm Y. As a reminder, the two compounds have 2 cardiac TnI epitopes and the carrier molecule is BSA. The obtaining of these bi-epitope compounds is described in Example 2. The comparison of the immunoreactivity of these compounds in the cardiac TnI immunoassay was carried out as described in Example 3 and the results are presented in Table 5 above and FIG. 3, which represents a graph giving the RFV fluorescence signals emitted by the

TABLE 5

Immunoreactivity of the bi-epitope compounds 1, 3, 4 and REF and of cardiac TnI peptide 1

| [c] peptide in ng/mL | REF compound (89 kDa) | | Compound 1 (94 kDa) Peptide 1 - BSA | | Noncoupled peptide 1 (28 kDa) | | Compound 3 (188 kDa) Peptide 1 - IgG | | Compound 4 (93 kDa) Peptide 5 - BSA | |
|---|---|---|---|---|---|---|---|---|---|---|
| | [c] | S | [c] | S | [c] | S | [c] | S | [c] | S |
| 0.5 | — | — | 5.3 | 270 | — | — | — | — | — | — |
| 1 | — | — | 11 | 451 | — | — | 5.3 | 175 | 11 | 60 |
| 2 | — | — | 21 | 935 | — | — | 11 | 360 | 21 | 118 |
| 5 | 56 | 62 | 53 | 1903 | — | — | 27 | 882 | 54 | 295 |
| 10 | 112 | 120 | 106 | 3606 | — | — | 53 | 1688 | 107 | 545 |
| 20 | 224 | 223 | 213 | 5911 | 713 | 2 | 106 | 3276 | 214 | 1100 |
| 50 | 559 | 617 | — | — | 1781 | 21 | 266 | 6209 | 535 | 2569 |
| 100 | 1118 | 997 | — | — | 3562 | 69 | — | — | — | — |
| 200 | 2236 | 1484 | — | — | 7125 | 356 | — | — | — | — |
| 500 | 5589 | 2102 | — | — | 17811 | 1825 | — | — | — | — |
| 1000 | 11179 | 2155 | — | — | 35623 | 3798 | — | — | — | — |
| 2000 | — | — | — | — | 71245 | 6140 | — | — | — | — |
| 4000 | — | — | — | — | 142491 | 7542 | — | — | — | — |

The abbreviation [c] corresponds to the concentration in µM of the compound. The abbreviation S corresponds to the signal in RFV.

various compounds, bi-epitope compound according to the prior art (REF Compound) and bi-epitope compounds according to the invention (Compounds 1 and 4), as a function of their concentration. The results show that compound 4 comprising GGGS and SGGG arms is less well recognized than compound 1 comprising Ado arms, but is much greater than the REF compound.

Example 6: Stability Tests

Compounds 1 and 2 were diluted to 3.75 ng/ml in the various buffers indicated in Table 6. A first assay was carried out on D0, the day on which the solutions were prepared. The values obtained served as a reference for monitoring the stabilities. The diluted solutions of the bi-epitope compounds were stored at +2/8° C. and assayed on D7 (7th day after preparation). Table 6 below presents the variation in the RFV signal of the immunoassay between D0 and D7 (Signal D7/Signal D0×100). Compounds 1 and 2 are stable and their antigenic properties are preserved when they are stored at +2/8° C. for 1 week.

TABLE 6

Stability of compounds 1 and 2 at +2/8° C. for 7 days

| Dilution buffer | Compound 1 | Compound 2 |
| --- | --- | --- |
| Citrate pH 5, 150 mM NaCl, 50 g/l BSA | 102% | 98% |
| Citrate pH 6, 150 mM NaCl, 50 g/l BSA | 99% | 95% |
| PBS, pH 6.2, 50 g/l BSA | 99% | 89% |

In a second step, a stability study of longer duration was carried out for compound 1 only, diluted in PBS, pH 6.2, containing 50 g/l of BSA. When stored at +2/8° C., compound 1 is stable in dilute solution: 97% of the signal of the immunoassay is found at 1 month storage, 94% at 3 months and 90% at 6 months. When stored at +18/25° C., compound 1 is stable in dilute solution for approximately 1 month (88% of the signal is found). It is also important to note that compound 1 is capable of withstanding at least three freezing/thawing cycles at −20° C. without any degradation of its antigenic properties. A higher number of freezing/thawing cycles was not tested.

All of these results demonstrate the excellent stability of the solutions of compound 1 according to the invention.

Example 7: Study of the Immunoreactivity of the Bi-Epitope Compound 5 According to the Invention Comprising a Mimotope The bi-epitope compound 5 was designed so as to operate as a control and/or standard and/or adjuster during a prodefensin A6 immunoassay. Compound 5 combines a linear epitope (QAEDDPLQAKL) and a mimotope (WTGVLSPTQEYR). The prodefensin A6 immunoassay was carried out using the VIDAS® automated immunoanalysis device (bioMérieux), according to the protocol described in application WO 2010/112777, namely using, as capture antibody, the 12H4E1 clone (bioMérieux), which recognizes the linear minimal epitope of sequence EDDPLQ, and, as detection antibody, the 1H8C9 clone (bioMérieux), the epitope of which is not linear but is a mimotope of sequence WTGVLSPTQEYR. These epitopes/mimotopes are those found in compound 5.

Table 7 below summarizes the fluorescence signals (RFV=relative fluorescence value) determined by the VIDAS® automated device when various concentrations of compound 5 (molecular molar mass: 98 155 Daltons) are tested. Compound 5 is indeed reactive in the prodefensin A6 immunoassay.

TABLE 7

Immunoreactivity of the bi-epitope compound 5

| [c] peptide in ng/ml | [c] in mM | RFV signal |
| --- | --- | --- |
| 17.5 | 0.2 | 385 |
| 35 | 0.4 | 583 |
| 175 | 1.8 | 1306 |
| 1750 | 18 | 2637 |
| 17 500 | 178 | 3448 |

LITERATURE REFERENCES

Boersma Y L and Plütckthun A, 2011, Curr. Opin. Biotechnol, 22: 849-857
Ellington A D and Szostak J W., 1990, Nature, 346: 818-822
Fields and Noble, 1990, Int J Pept Protein Res., 35:161-214
Merrifield 1963, J Am Chem Soc. 85:2149-2154
Shan S. Wong, 1991, Chemistry of Protein Conjugation and Cross-linking», CRC Press Inc., Boca Raton, Fla., United States

The invention claimed is:

1. An immunoassay system comprising one or more antibodies for binding an analyte and a bi-epitope compound of formula (I) as a control or standard:

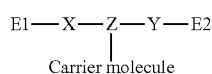

(I)

wherein:
E1 represents SEQ ID NO: 1 or SEQ ID NO: 3;
E2 represents SEQ ID NO: 2;
X and Y each represent a dimer of 8-amino-3,6-dioxaoctanoic acid;
the carrier molecule is bovine serum albumin or immunoglobulin G; and
Z represents a cysteine bonded with the carrier molecule.

2. The immunoassay system as claimed in claim 1, wherein the carrier molecule is bovine serum albumin.

3. The immunoassay system as claimed in claim 2, wherein E1 represents SEQ ID NO: 1.

4. The immunoassay system as claimed in claim 2, wherein E1 represents SEQ ID NO: 3.

5. The immunoassay system as claimed in claim 1, wherein the carrier molecule is immunoglobulin G and E1 represents SEQ ID NO: 1.

6. An immunoassay system comprising one or more antibodies for binding an analyte and a bi-epitope compound of formula (I) as a control or standard:

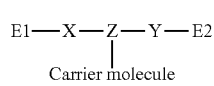 (I)

wherein:
E1 represents SEQ ID NO: 1;
E2 represents SEQ ID NO: 2;
X represents SEQ ID NO: 25;
Y represents SEQ ID NO: 26;
the carrier molecule is bovine serum albumin; and
Z represents a cysteine bonded with the carrier molecule.

7. An immunoassay system comprising one or more antibodies for binding an analyte and a bi-epitope compound of formula (I) as a control or standard:

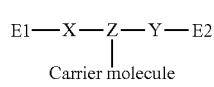 (I)

wherein:
E1 represents SEQ ID NO: 23;
E2 represents SEQ ID NO: 5;
X and Y each represent a dimer of 8-amino-3,6-dioxaoctanoic acid;
the carrier molecule is bovine serum albumin; and
Z represents a cysteine bonded with the carrier molecule.

* * * * *

SEQUENCE LISTING

<160> NUMBER OF SEQ ID NOS: 30

<210> SEQ ID NO 1
<211> LENGTH: 9
<212> TYPE: PRT
<213> ORGANISM: Artificial Sequence
<220> FEATURE:
<223> OTHER INFORMATION: epitope

<400> SEQUENCE: 1

Ala Thr Glu Pro His Ala Lys Lys Lys
1               5

<210> SEQ ID NO 2
<211> LENGTH: 11
<212> TYPE: PRT
<213> ORGANISM: Artificial Sequence

```
<220> FEATURE:
<223> OTHER INFORMATION: epitope

<400> SEQUENCE: 2

Ala Gly Leu Gly Phe Ala Glu Leu Gln Asp Leu
1               5                   10

<210> SEQ ID NO 3
<211> LENGTH: 12
<212> TYPE: PRT
<213> ORGANISM: Artificial Sequence
<220> FEATURE:
<223> OTHER INFORMATION: epitope

<400> SEQUENCE: 3

Lys Ile Ser Ala Ser Arg Lys Leu Gln Leu Lys Thr
1               5                   10

<210> SEQ ID NO 4
<211> LENGTH: 12
<212> TYPE: PRT
<213> ORGANISM: Artificial Sequence
<220> FEATURE:
<223> OTHER INFORMATION: epitope

<400> SEQUENCE: 4

Asn Tyr Val Thr Pro Pro Trp Ala Ile Phe Arg His
1               5                   10

<210> SEQ ID NO 5
<211> LENGTH: 12
<212> TYPE: PRT
<213> ORGANISM: Artificial Sequence
<220> FEATURE:
<223> OTHER INFORMATION: epitope

<400> SEQUENCE: 5

Trp Thr Gly Val Leu Ser Pro Thr Gln Glu Tyr Arg
1               5                   10

<210> SEQ ID NO 6
<211> LENGTH: 12
<212> TYPE: PRT
<213> ORGANISM: Artificial Sequence
<220> FEATURE:
<223> OTHER INFORMATION: epitope

<400> SEQUENCE: 6

Ser His Leu Thr Pro Pro Trp Met Asp Tyr Arg Val
1               5                   10

<210> SEQ ID NO 7
<211> LENGTH: 12
<212> TYPE: PRT
<213> ORGANISM: Artificial Sequence
<220> FEATURE:
<223> OTHER INFORMATION: epitope

<400> SEQUENCE: 7

Val Met Ala Val Thr Cys Ser Thr Cys Asp Ser Arg
1               5                   10

<210> SEQ ID NO 8
<211> LENGTH: 12
<212> TYPE: PRT
<213> ORGANISM: Artificial Sequence
<220> FEATURE:
```

```
<223> OTHER INFORMATION: epitope

<400> SEQUENCE: 8

Leu Thr Pro Pro Thr Glu Asp Leu Arg Pro Pro Asp
1               5                   10

<210> SEQ ID NO 9
<211> LENGTH: 12
<212> TYPE: PRT
<213> ORGANISM: Artificial Sequence
<220> FEATURE:
<223> OTHER INFORMATION: epitope

<400> SEQUENCE: 9

Tyr Gly Asn His Ser Cys Thr His Ile Gly His Cys
1               5                   10

<210> SEQ ID NO 10
<211> LENGTH: 12
<212> TYPE: PRT
<213> ORGANISM: Artificial Sequence
<220> FEATURE:
<223> OTHER INFORMATION: epitope

<400> SEQUENCE: 10

Gly Pro Ser Tyr Thr Cys Leu His Phe Gly His Cys
1               5                   10

<210> SEQ ID NO 11
<211> LENGTH: 12
<212> TYPE: PRT
<213> ORGANISM: Artificial Sequence
<220> FEATURE:
<223> OTHER INFORMATION: epitope

<400> SEQUENCE: 11

Thr Glu Arg Glu Val His Asn Trp Phe Pro Phe His
1               5                   10

<210> SEQ ID NO 12
<211> LENGTH: 12
<212> TYPE: PRT
<213> ORGANISM: Artificial Sequence
<220> FEATURE:
<223> OTHER INFORMATION: epitope

<400> SEQUENCE: 12

Tyr Pro His Pro Trp Ser Met His Val Ile Arg Ala
1               5                   10

<210> SEQ ID NO 13
<211> LENGTH: 12
<212> TYPE: PRT
<213> ORGANISM: Artificial Sequence
<220> FEATURE:
<223> OTHER INFORMATION: epitope

<400> SEQUENCE: 13

Thr Thr Thr Pro His Pro Trp Ala Leu Phe Ala Val
1               5                   10

<210> SEQ ID NO 14
<211> LENGTH: 12
<212> TYPE: PRT
<213> ORGANISM: Artificial Sequence
<220> FEATURE:
<223> OTHER INFORMATION: epitope
```

<400> SEQUENCE: 14

Thr Pro His Pro Trp Gln Arg Trp Val Val Tyr Ser
1               5                   10

<210> SEQ ID NO 15
<211> LENGTH: 12
<212> TYPE: PRT
<213> ORGANISM: Artificial Sequence
<220> FEATURE:
<223> OTHER INFORMATION: epitope

<400> SEQUENCE: 15

Glu Asp Val Leu Arg Trp His Pro Glu Trp Pro Gly
1               5                   10

<210> SEQ ID NO 16
<211> LENGTH: 12
<212> TYPE: PRT
<213> ORGANISM: Artificial Sequence
<220> FEATURE:
<223> OTHER INFORMATION: epitope

<400> SEQUENCE: 16

Tyr His Glu Thr Trp Pro Pro Lys Ser Ala Gln Leu
1               5                   10

<210> SEQ ID NO 17
<211> LENGTH: 12
<212> TYPE: PRT
<213> ORGANISM: Artificial Sequence
<220> FEATURE:
<223> OTHER INFORMATION: epitope

<400> SEQUENCE: 17

Tyr His Asp Asn Trp Pro Gln Pro Ser Arg Ser Trp
1               5                   10

<210> SEQ ID NO 18
<211> LENGTH: 12
<212> TYPE: PRT
<213> ORGANISM: Artificial Sequence
<220> FEATURE:
<223> OTHER INFORMATION: epitope

<400> SEQUENCE: 18

Gln His Asn His Gln Arg His Gly Ala Met Gly Ala
1               5                   10

<210> SEQ ID NO 19
<211> LENGTH: 12
<212> TYPE: PRT
<213> ORGANISM: Artificial Sequence
<220> FEATURE:
<223> OTHER INFORMATION: epitope

<400> SEQUENCE: 19

Tyr His Asp Met Trp Pro Met Ser Gly Arg Met Ala
1               5                   10

<210> SEQ ID NO 20
<211> LENGTH: 12
<212> TYPE: PRT
<213> ORGANISM: Artificial Sequence
<220> FEATURE:
<223> OTHER INFORMATION: epitope

```
<400> SEQUENCE: 20

Tyr His Asp Asn Trp Pro Leu Asn Gly Ala Arg
1               5                   10

<210> SEQ ID NO 21
<211> LENGTH: 12
<212> TYPE: PRT
<213> ORGANISM: Artificial Sequence
<220> FEATURE:
<223> OTHER INFORMATION: epitope

<400> SEQUENCE: 21

Tyr His Asp Met Trp Pro Ala Ile Gln Leu Ser Pro
1               5                   10

<210> SEQ ID NO 22
<211> LENGTH: 12
<212> TYPE: PRT
<213> ORGANISM: Artificial Sequence
<220> FEATURE:
<223> OTHER INFORMATION: epitope

<400> SEQUENCE: 22

Tyr His Glu Lys Phe Pro Gly Pro Val Val Leu Pro
1               5                   10

<210> SEQ ID NO 23
<211> LENGTH: 10
<212> TYPE: PRT
<213> ORGANISM: Artificial Sequence
<220> FEATURE:
<223> OTHER INFORMATION: epitope

<400> SEQUENCE: 23

Gln Ala Glu Asp Asp Pro Leu Gln Ala Lys
1               5                   10

<210> SEQ ID NO 24
<211> LENGTH: 29
<212> TYPE: PRT
<213> ORGANISM: Artificial Sequence
<220> FEATURE:
<223> OTHER INFORMATION: peptide

<400> SEQUENCE: 24

Ala Thr Glu Pro His Ala Lys Lys Lys Gly Gly Ser Cys Ser Gly
1               5                   10                  15

Gly Gly Ala Gly Leu Gly Phe Ala Glu Leu Gln Asp Leu
            20                  25

<210> SEQ ID NO 25
<211> LENGTH: 4
<212> TYPE: PRT
<213> ORGANISM: Artificial Sequence
<220> FEATURE:
<223> OTHER INFORMATION: arms

<400> SEQUENCE: 25

Gly Gly Gly Ser
1

<210> SEQ ID NO 26
<211> LENGTH: 4
<212> TYPE: PRT
<213> ORGANISM: Artificial Sequence
<220> FEATURE:
```

```
<223> OTHER INFORMATION: arms

<400> SEQUENCE: 26

Ser Gly Gly Gly
1

<210> SEQ ID NO 27
<211> LENGTH: 6
<212> TYPE: PRT
<213> ORGANISM: Artificial Sequence
<220> FEATURE:
<223> OTHER INFORMATION: arms

<400> SEQUENCE: 27

Gly Ser Gly Ser Gly Ser
1               5

<210> SEQ ID NO 28
<211> LENGTH: 6
<212> TYPE: PRT
<213> ORGANISM: Artificial Sequence
<220> FEATURE:
<223> OTHER INFORMATION: arms

<400> SEQUENCE: 28

Ser Gly Ser Gly Ser Gly
1               5

<210> SEQ ID NO 29
<211> LENGTH: 10
<212> TYPE: PRT
<213> ORGANISM: Artificial Sequence
<220> FEATURE:
<223> OTHER INFORMATION: peptide

<400> SEQUENCE: 29

Ala Thr Glu Pro His Ala Lys Lys Lys Cys
1               5                   10

<210> SEQ ID NO 30
<211> LENGTH: 12
<212> TYPE: PRT
<213> ORGANISM: Artificial Sequence
<220> FEATURE:
<223> OTHER INFORMATION: peptide

<400> SEQUENCE: 30

Ala Gly Leu Gly Phe Ala Glu Leu Gln Asp Leu Cys
1               5                   10
```